United States Patent [19]

Field et al.

[11] 4,388,306

[45] Jun. 14, 1983

[54] PHARMACEUTICAL COMPOSITION COMPRISING MODIFIED POLYRIBOINOSINIC-POLYRIBOCYTIDYLIC ACID, FOR INDUCTION OF INTERFERON IN PRIMATES

[75] Inventors: A. Kirk Field, North Wales; Alfred A. Tytell, Lansdale; George P. Lampson, Hatfield, all of Pa.

[73] Assignee: Merck & Co., Inc., Rahway, N.J.

[21] Appl. No.: 346,673

[22] Filed: Feb. 8, 1982

Related U.S. Application Data

[63] Continuation of Ser. No. 156,295, Jun. 4, 1980, abandoned, which is a continuation-in-part of Ser. No. 76,004, Sep. 17, 1979, abandoned.

[51] Int. Cl.³ ................. A61K 37/02; A61K 45/02
[52] U.S. Cl. ...................... 424/177; 424/85; 424/180; 536/28; 536/29
[58] Field of Search .............. 536/28, 88, 29; 424/180, 85, 177; 260/112.5 R

[56] References Cited

U.S. PATENT DOCUMENTS

| | | | |
|---|---|---|---|
| 3,679,654 | 7/1972 | Maes | 536/28 |
| 3,725,545 | 4/1973 | Maes | 536/28 |
| 3,952,097 | 4/1976 | Levy | 536/22 |
| 4,024,222 | 5/1977 | Ts'o et al. | 536/29 |
| 4,130,641 | 12/1978 | Ts'o et al. | 536/28 |

OTHER PUBLICATIONS

Carrol, Biochemistry, vol. 11, pp. 426–433, (1972).
Haynes, Biochemistry, vol. 9. pp. 4410–4416, (1970).
Catalona, Pro. Soc. Exp. Bio. & Med., vol. 140, pp. 66–71, (1972).
Wacker, Archiv. fur die gesamte Virusforschung, vol. 36, pp. 71–79, (1972).

*Primary Examiner*—Blondel Hazel
*Attorney, Agent, or Firm*—Frank M. Mahon; Gabriel Lopez; Hesna J. Pfeiffer

[57] ABSTRACT

A complex of polyriboinosinic-polyribocytidylic acid (poly I:C) with poly-L-lysine hydrobromide ([lysine.HBr]$_n$) having a defined molecular weight is prepared which is about 5–15 times as resistant to hydrolysis by pancreatic ribonuclease as the parent poly I:C. A pharmaceutical solution, containing a relatively high concentration of the complex, prepared as described, induces significant antiviral levels of serum interferon in monkeys under conditions in which poly I:C itself induces little or no interferon. An important feature of this invention is that the product is a soluble material requiring no special solubilizing agent, thereby facilitating the preparation of solutions having the desired concentration. The product will hereinafter be designated as poly I:C/poly-L-lysine.

6 Claims, No Drawings

PHARMACEUTICAL COMPOSITION COMPRISING MODIFIED POLYRIBOINOSINIC-POLYRIBOCYTIDYLIC ACID, FOR INDUCTION OF INTERFERON IN PRIMATES

RELATIONSHIP TO PRIOR APPLICATIONS

This is a continuation of application Ser. No. 156,295, filed June 4, 1980, now abandoned which is a continuation-in-part of U.S. application Ser. No. 76,004 filed Sept. 17, 1979, now abandoned.

BACKGROUND OF THE INVENTION

The synthetic double-stranded RNA, polyriboinosinic-polyribocytidylic acid (poly I:C), is effective as an interferon inducer in rodents and rabbits and as such provides protection against a variety of RNA and DNA viruses in these species [A. K. Field et al., *Proc. Natl. Acad. Sci.* U.S.A., 58, pp. 1004–1010, (1967)]. However, poly I:C shows only a very weak capacity to induce interferon in man and non-human primates.

It has been stated that enzymatic inactivation of poly I:C is the reason for its poor capacity to induce interferon in primates [H. B. Levy et al., *J. Inf. Dis.*, 132, p. 434 (1975)]. These authors have reported the preparation of a solubilized formulation of poly I:C and poly-L-lysine (molecular weight 2000 to 5000) in carboxymethylcellulose (CMC) as the solubilizing agent [see also Levy, U.S. Pat. No. 3,952,097 (1976)]. This complex is relatively resistant to ribonuclease and induces significant quantities of interferon in rhesus monkeys, chimpanzees and man.

However, certain disadvantages are associated with CMC. It is a polysaccharide which is at best poorly biodegradable and on repeated injection may cause deposition of residues which may cause irritations (pathology). In addition, CMC has been considered to be a potential carcinogen. Both the sodium and ammonium salts of CMC appear on the NIOSH Suspected Carbinogen List, U.S. Environmental Protection Agency, Office of Toxic Substances, March, 1976. The references upon which these listings were made are: A. L. Walpole, *Morphol. Precursors Cancer*, Proc. Inter. Conf. Perugia, Italy, pp. 83–88, 1961 (Publ. 1962) and *Rev. Canad. Biol.* (Mont.), 20, pp. 701 (1961).

SUMMARY OF THE INVENTION

In the present invention a combination of poly I:C (having a high molecular weight) with poly-L-lysine hydrobromide (having a high molecular weight) have been prepared in such a molar ratio as to preclude the need for a solubilizing agent in a pharmaceutical solution of relatively high concentration. Our preparations of poly I:C/poly-L-lysine hydrobromide are superior inducers of antiviral levels of interferon in primates. The combination is prepared so that the molar ratio of poly I:C to poly-L-lysine hydrobromide (or poly-L-lysine hydrochloride) is about 2 to 1 (calculated as ratio of nucleotide residue to lysine residue). Since the peptide hydrobromide is generally hygroscopic, on a moisture-free basis (of the peptide) the best complex may be prepared by mixing by weight one part of poly I:C with 0.31 parts of poly-L-lysine hydrobromide. Viscosity and solubility considerations limit the concentration of ingredients per ml that may be prepared. In practice the concentration of poly I:C per ml is used at from about 1-2 mg/ml. This requires a theoretical amount of from about 0.31 to 0.62 mg of dry poly-L-lysine hydrobromide, respectively. [In practice, the ratio of poly I:C to poly-L-lysine hydrobromide is such as to yield a complex at the limit of solubility.] The vehicle used is isotonic, pyrogen-free phosphate buffered saline (pH 7.2) although any suitable physiologically acceptable vehicle may be used. Although the hydrobromide and hydrochloride salts of the peptide are described, other suitable acids can be used.

The combination of poly I:C and poly-L-lysine hydrobromide is prepared by mixing a solution of poly I:C of known concentration and suitable molecular weight with a solution of poly-L-lysine hydrobromide of known concentration and suitable molecular weight. The solutions are each prepared in phosphate buffered saline. When the two solutions are mixed a precipitate appears which will go into solution (become soluble) with mixing at room temperature or at 2°–8° C. in approximately 72 hours, although a small amount of undissolved solids (less than 2% of the ingredients) may be present. The solution is clarified by filtration through suitable glass or membrane filters to yield a homogeneous solution.

The solution of poly I:C is prepared by mixing solutions of equimolar quantities of the individual homopolynucleotides, poly I and poly C, to a final concentration of about 2 mg/ml. The complex is characterized prior to addition of the poly-L-lysine.HBr.

The poly I used has the following properties:

| | |
|---|---|
| Ultraviolet spectrum | Satisfactory |
| Absorption maximum | 248 nm |
| Absorption minimum | 225 nm |
| Extinction coefficient ($E_{1\%}$) at 248 nm | 240 |
| Nucleotide content | 2.4 μM/mg |
| Sedimentation coefficient (Sw, 20) | 19.2 |

The poly C used has the following properties:

| | |
|---|---|
| Ultraviolet spectrum | Satisfactory |
| Absorption maximum | 268 nm |
| Absorption minimum | 249 nm |
| Extinction coefficient ($E_{1\%}$) at 248 nm | 177 |
| Nucleotide content | 2.95 μM/mg |
| Sedimentation coefficient (Sw, 20) | 5.0 |

The poly-L-lysine.HBr used has the following properties:

| | |
|---|---|
| Molecular weight | 32,500 |
| Degree of polymerization (D.P.) | 155 residues |
| Lysine content (% of theoretical) | 89.7 (of net weight) |
| Bromide content (% of theoretical) | 87.2 (of net weight) |
| Other amino acids | None |

The poly I:C, prepared from the above poly I and poly C, has the following properties:

| | |
|---|---|
| Ultraviolet spectrum | Satisfactory |
| Absorption maximum | 248, 265 nm |
| Absorption minimum | 228 nm |
| Extinction coefficient ($E_{1\%}$) at 265 nm | 145 |
| Hypochromicity at 248 nm | 35.5% |

| -continued | |
|---|---|
| Thermal denaturation midpoint (Tm) | 64° C. |
| Hyperchromicity on thermal denaturation | 77.8% |
| Sedimentation coefficient (Sw, 20) | 11.0 |
| Relative viscosity | 1.59 |

The poly I:C/poly-L-lysine prepared from the above poly I, poly C, and poly-L-lysine, has the following properties:

| | |
|---|---|
| Ultraviolet spectrum | Satisfactory |
| Absorption maximum | 248, 265 nm |
| Absorption minimum | 230 nm |
| Extinction coefficient ($E_{1\%}$) at 265 nm | 140 |
| Thermal denaturation midpoint (Tm) | 83° C. |
| Hyperchromicity on thermal denaturation | 109% at 83° C., <10 at 64° C. |
| Sedimentation coefficient (Sw, 20) | 11.5 |
| Relative viscosity | 1.65 |
| Ribonuclease resistance compared to that of poly I:C | 14.0% |
| Conductivity | 7.1 millimhos |
| Nominal poly I:C concentration | 1.0 mg/ml |
| Actual measured poly I:C concentration | 1.0 mg/ml |
| Nominal poly-L-lysine concentration | 0.310 mg/ml |
| Actual measured poly-L-lysine concentration | 0.330 mg/ml |

There is same degree of variability in the chemical characteristics of the components, see the following table of ranges:

| | ($E_{1\%}$ at 248 nm) | (Sw, 20) | Molecular weight |
|---|---|---|---|
| Poly I | 240–280 | 11–20 | — |
| Poly C | 175–185 | 5–7 | — |
| Poly L-lysine | — | — | 10,000–70,000 preferably 10,000 to 35,000 |

The compositions prepared by this invention are useful in inducing antiviral levels of interferon in mammalian and other animal systems where uncomplexed poly I:C is not an efficient inducer of interferon. For example, in grivet monkeys, poly I:C/poly-L-lysine injected intravenously at one milligram per kilogram weight equivalent of poly I:C results in the induction of high titered circulating interferon. At a level of 0.25 mg equivalent of poly I:C substantial circulating interferon titers are achieved. Uncomplexed poly I:C injected at these dosage levels stimulates low or no detectable serum interferon.

Although the complex of this invention has not yet been administered to humans, by analogy to other similar compositions, the preferred dosage range for humans of the poly I:C/poly-L-lysine complex may be as high as 0.3–0.4 mg/kg body weight, administered as for instance on a daily basis by IV injection. Initial doses can be as low as 10 μg/kg body weight daily.

PREFERRED EMBODIMENTS

Example 1

Preparation of Solutions of Poly I:C and Poly-L-lysine Hydrobromide (Lot 827)

From the calculated extinction coefficient a solution containing 2.16 mg/ml of polyriboinosinic acid (poly I) as defined above in phosphate buffered saline, was obtained by heating in an 80° C. water bath. The heated solution was sterilized by filtration through a 0.45μ membrane.

From the calculated extinction coefficient a solution containing 2 mg/ml of polyribocytidylic acid (poly C), as defined above in phosphate buffered saline, was obtained by stirring at ambient temperature. The poly C solution was sterilized by filtration through a 0.45μ filter membrane.

Equal volumes of poly I and poly C were mixed with stirring in an 80° C. water bath until a clear solution was obtained. The mixture was then allowed to cool slowly at ambient temperature in order to anneal the poly I and poly C with the formation of poly I:C.

A solution of poly-L-lysine hydrobromide was prepared to contain on a dry weight basis 0.62 mg/ml in phosphate buffered saline by stirring into solution at ambient temperature. The clear solution was sterilized by filtration through a 0.2μ membrane. The preparation of poly-L-lysine whuch was used was demonstrated by appropriate analytical procedures to contain equimolar content of L-lysine and bromine (the poly-L-lysine hydrobromide should be construed to have a composition as follows: $[lysine.HBr]_n$—where n is the degree of polymerization), and a molecular weight as defined.

EXAMPLE 2

Preparation of Poly I:C/Poly-L-lysine (lot 827)

Equal volumes of poly I:C (2.08 mg/ml) prepared as set forth in Example 1 and poly-L-lysine hydrobromide (0.62 mg/ml) prepared as set forth in Example 1 were mixed with stirring. Stirring was continued for 48–72 hours at 2°–8° C. until only a trace of undissolved material remained. The viscous solution was clarified by filtration through a sterile clarifying membrane. The filtered solution was dispensed into ampoules and kept at 2°–8° C. until used. The filtered solution was demonstrated by appropriate analytical procedures to contain greater than 98% of the nominal concentration of complexed poly I:C/poly-L-lysine hydrobromide. All of the poly-L-lysine was demonstrated by appropriate sedimentation experiments to be bound to the poly I:C. The ribonuclease resistance of the poly I:C in the complex was increased 5–15 fold over the parent poly I:C. The thermal transition mid-point (Tm) was increased from 64° C. (for the poly I:C alone) to 82°–83° C. for the complex when measured in 0.15 molar NaCl. The measurements were made by appropriate standard spectrophotometric measurements of hyperchromicity.

The following summarizes the physical characteristics of this preparation of poly I:C/poly-L-lysine, Lot 827:

| | |
|---|---|
| Ultraviolet spectrum | Satisfactory |
| Absorption maximum | 248, 265 nm |
| Absorption minimum | 230 nm |
| Extinction coefficient ($E_{1\%}$) at 265 nm | 140 |
| Thermal denaturation point (Tm) | 83° C. |
| Hyperchromicity on thermal denaturation at 64° C. at 83° C. | <10% 109% |
| Sedimentation coefficient (Sw, 20) | 11.5 |
| Relative viscosity | 1.65 |
| Nominal measure poly I:C concentration | 1.0 mg/ml |
| Nominal poly-L-lysine | |

EXAMPLE 3

Interferon Induction in Grivet Monkeys (Cercopithecus aethiops)

Poly I:C alone or combined with poly-L-lysine as set forth in Examples 1 and 2 were prepared and injected intravenously at 1.0 mg (as poly I:C)/kg body weight into grivet monkeys. Blood samples were obtained from animals prior to injection (prebled at time 0 hours) and at intervals thereafter. Interferon titers were determined by assay of serial dilutions of serum samples for reduction of infection of cell cultures by vesicular stomatitis virus. Peak interferon titers were obtained at approximately eight hours after injection. Characterization of the poly I:C complexes included measurement of the resistance to hydrolysis by pancreatic ribonuclease and the thermal transition midpoint (Tm) (e.g., the temperature at which half of the poly I:C has separated into the individual polynucleotides, poly I and poly C) as evidenced by hyperchromicity. Data are presented in Table 1. Peak interferon titers at least 10–100 fold greater than those obtained from monkeys induced with poly I:C alone, were obtained from monkeys induced with poly I:C complexed with poly-L-lysine.

-continued

| concentration | 0.310 mg/ml |
|---|---| body weight. Samples of blood were taken immediately prior to and 8 hours post injection. Serum prepared from these samples was assayed for interferon. Resistance to ribonuclease was significantly increased in all samples measured including the molecular weight range from 1050 through approximately 9000–10,000. The thermal transition midpoint was significantly raised at all molecular weights of poly-L-lysine. Interferon induction was enhanced only marginally (geometric mean titer range 50–200) with poly-L-lysines of molecular weights up through approximately 10,000. At molecular weights above 10,000 there was a sharp rise in enhancement of interferon induction with a range of geometric mean interferon titers of 529 to 1988. These data are presented in Table 2.

TABLE 1

INDUCTION OF INTERFERON IN GRIVET MONKEYS

| Inducer | Ratio (wt/wt) Poly I:C/ Poly-L-lysine Hydrobromide | Relative RNase Sensitivity | Thermal Transition Midpoint (Tm)[a] | Geometric Mean Titer International Units/ml Serum Interferon Titer 0 hrs. | 8 hrs. |
|---|---|---|---|---|---|
| Poly I:C | — | 100 | 64° C. | 10 | 48 |
| Poly I:C. Poly-L-lysine Hydrobromide | 1:0.31 | 16 | 82 | 9 | 1550 |

[a]solvent 0.15m NaCl - 0.006M phosphate buffer, pH 7.2

TABLE 2

| POLY I:C/POLY-L-LYSINE.HBr INTERFERON INDUCER | | GRIVET MONKEY GEOMETRIC MEAN INTERFERON TITER (International units/ml) | | |
|---|---|---|---|---|
| Poly-L-lysine.HBr Mol. Wt. | Relative RNase Sensitivity | Thermal Transition Midpoint (°C.) | Time (hours) | |
| | | | $T_0$ | $T_8$ | $T_8-T_0$ |
| — | 100 | 64.0 | 10 | 48 | 38 |
| 1050 | 20.8 | 66.0 | 7 | 80 | 73 |
| 3760 | 2.8 | 78.5 | 29 | 230 | 201 |
| 4590 | 3.9 | 80.5 | 10 | 160 | 150 |
| 5850 | 3.2 | 80.5 | 5 | 56 | 51 |
| 9-10000 | 21.6 | 81.0 | 10 | 112 | 102 |
| 5-15000 | 18.0 | 74.0 | 20 | 1290 | 1270 |
| 20-22000 | — | — | 20 | 910 | 890 |
| 15-30000 | 11.4 | 81.0 | 12 | 2000 | 1988 |
| 32500 | 16.0 | 82.0 | 9 | 1550 | 1541 |
| >20000 | — | — | 7 | 536 | 529 |
| >70000 | 14.3 | 85.0 | 5 | 1300 | 1295 |

EXAMPLE 4

Comparison of Interferon Induction in Grivet Monkeys Using poly I:C Complexed with poly-L-lysines of Various Molecular Weights Complexes of poly I:C/poly-L-lysine.HBr were prepared using samples of poly-L-lysine.HBr of defined molecular weight ranges. These complexes were compared for their capacity to induce interferon in grivet monkeys as described in Example 3. Ribonuclease sensitivity and thermal transition midpoints were determined for each of the complexes where feasible. All monkeys were injected intravenously with 1 mg (as poly I:C)/kg

What is claimed is:

1. An interferon-inducing composition comprising a solution in a pharmaceutically acceptable aqueous carrier, of a complex of poly I:C/poly-L-lysine hydrobromide or hydrochloride, the concentration in solution of the poly I:C being from about 1 to about 2 mg/ml, the ratio by dry weight of the poly I:C to the poly-L-lysine hydrobromide or hydrochloride being about 1 to about 0.3, or a molar ratio of 2:1; the poly I having a $S_w 20°$ of 11–20, and an $E_{1\%}$ at 248 nm of 240–280; the poly C having a $S_w 20°$ of 5–7 and an $E_{1\%}$ at 248 nm of 175–185; and the poly-L-lysine having a molecular weight of from about 10,000 to about 70,000 daltons.

2. The composition of claim 1 in which the poly I:C concentration is about 1 mg/ml.

3. The composition of claim 1 in which the poly-L-lysine is in the hydrobromide form.

4. The composition of claim 3 in which the molecular weight of the poly-L-lysine hydrobromide is from about 10,000 to about 35,000 daltons.

5. The composition of claim 1 wherein the poly I has a $S_w 20°$ of about 19 and an $E_{1\%}$ at 248 nm of 240.

6. The composition of claim 1 wherein poly C has a $S_w 20°$ of about 5 and an $E_{1\%}$ at 248 of 177.

* * * * *